United States Patent [19]
Ludwig et al.

[11] Patent Number: 5,900,358
[45] Date of Patent: May 4, 1999

[54] METHOD FOR NON-RADIOACTIVE GEL SHIFT ASSAYS

[76] Inventors: Linda Besante Ludwig, 861 Main St.; Barbara J. Hughes, 472 Linden Ave., both of East Aurora, N.Y. 14052

[21] Appl. No.: 08/899,868

[22] Filed: Jul. 24, 1997

[51] Int. Cl.[6] ..................................................... C12Q 1/68
[52] U.S. Cl. ............................... 435/6; 436/501; 935/77; 935/78
[58] Field of Search ................................. 435/6; 436/501; 536/23.1, 24.1, 24.3–33, 25.4; 935/77, 78

[56] References Cited

U.S. PATENT DOCUMENTS 4,888,274  12/1989  Radding et al. ............................ 435/6
5,273,881  12/1993  Sena et al. ................................. 425/6

OTHER PUBLICATIONS

Matthews et al. (1988) Analytized Biochemisty, vol. 169, pp. 1–25.
Suske et al., "Non–radioactive Method to Visualize Specific DNA–Protien Interactions in the Band Shift Assay", Nucleic Acids Research, vol. 17, No. 11, p. 4405, 1989.

Primary Examiner—Ardin H. Marschel
Attorney, Agent, or Firm—Hodgson, Russ, Andrews, Woods & Goodyear, LLP

[57] ABSTRACT

A method for a non-radioactive electrophoretic mobility shift assay performed with non-radioactive labeled dsDNA, non-radioactive labeled ssDNA or non-radioactive labeled RNA probes interacting with a nucleic acid binding protein in forming a complex, electrophoresing the mixture containing the complex, transferring the complex to a membrane, and detecting the complex transferred to the membrane by detecting the non-radioactive label in the complex.

8 Claims, 4 Drawing Sheets

METHOD FOR NON-RADIOACTIVE GEL SHIFT ASSAYS

This application is a nonprovisional of our co-pending U.S. application Ser. No. 60/022,688, filed Jul. 26, 1996, the disclosure of which is herein incorporated by reference.

BACKGROUND OF THE INVENTION

Gel retardation or electrophoretic mobility shift assay (EMSA) is a useful method for visualizing specific interactions between DNA-binding proteins and DNA. DNA-binding proteins are involved in a variety of cellular processes ranging from transcription and replication to recombination and viral integration. Typically, $^{32}$P-labeled DNA probes containing the sequence bound by the protein of interest are used in mobility shift assays, but a non-radioactive method using DNA labeled with digoxygenin-dUTP has previously been described (Suske et al., 1989, *Nucleic Acids Res.* 17:4405). While hybridization of non-radioactive labeled probes has been employed in Southern or Northern analysis, and other than the method described by Suske et al., use of non-radioactive labeled probes directly for studying protein-polynucleotide interactions with EMSA has not previously been described.

SUMMARY OF THE INVENTION

Using the non-radioactive method of the present invention, nucleic acid molecules tested as molecular probes include a range of DNA sizes, from a 63mer Oct-1 binding site to a 690 bp dsDNA sequence containing the HIV-1 long terminal repeat (LTR); as well as biotinylated ssDNA and RNA probes (FIG. 1). Biotinylation of RNA, ssDNA or dsDNA probes is easily performed, and the resultant probe is stable and sensitive, with none of the hazards of handling and disposing of radioactively-labeled oligonucleotide probes. EMSA can be performed in a standard fashion, but further includes the embodiments described herein for detection of the non-radioactive labeled probe, as described below, and as depicted in the appended figures showing non-radioactive labeled dsDNA, ssDNA or RNA interaction with protein analyzed using EMSA.

DETAILED DESCRIPTION

Figure 1:
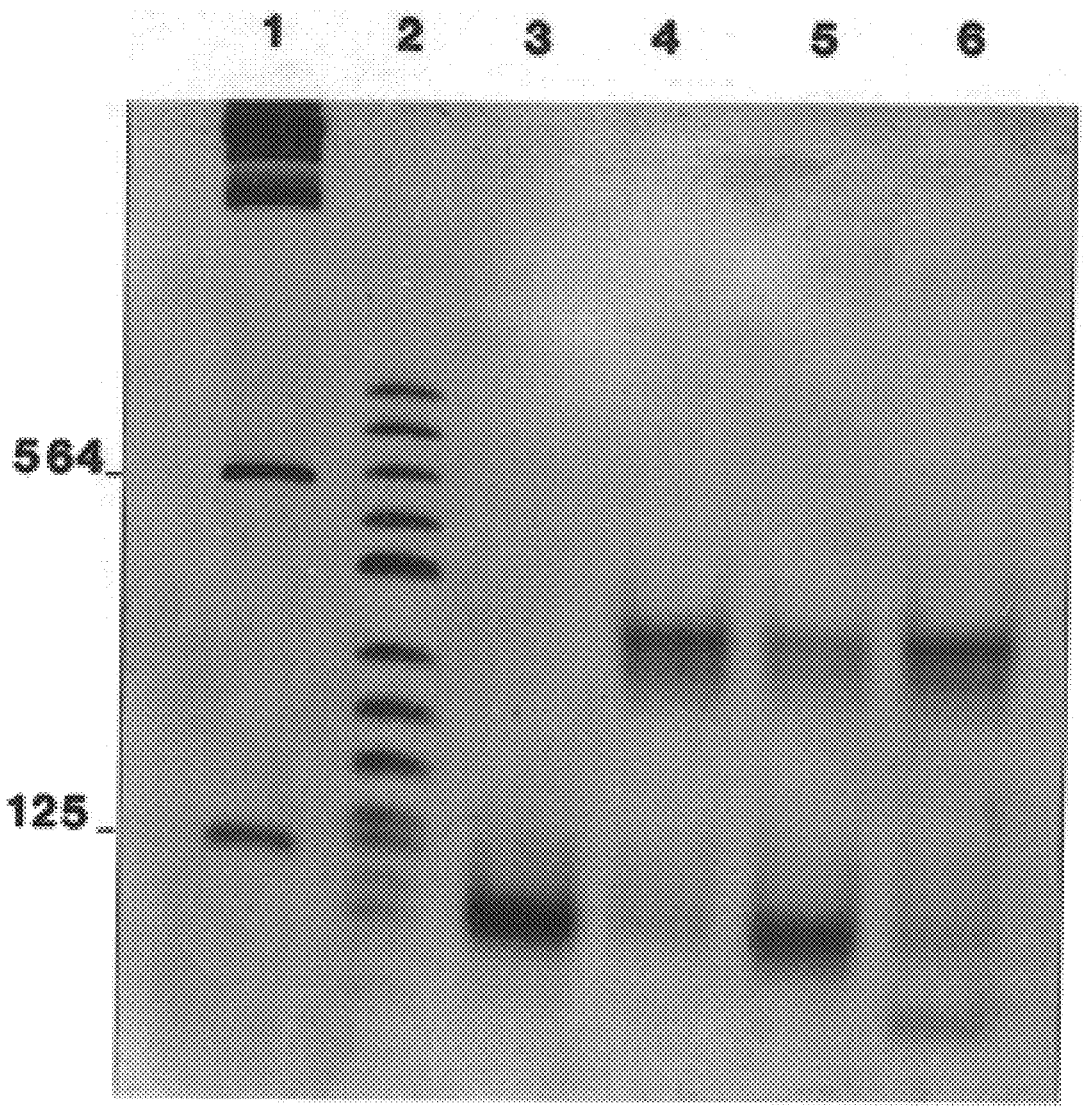
FIG. 1: Specificity of EBNA-1 DNA and EBNA-1 protein interaction is demonstrated by competition. Biotinylated EBNA-1 DNA (82mer) was incubated alone (lane 3) or with EBNA-1 protein extract (lanes 4–6) and in the presence of 30 ng unlabeled competitor DNA (EBNA-1 in lane 5 or Oct-1 DNA in lane 6). Molecular weight standards comprise biotinylated X HindIII digest (lane 1), and biotinylated low molecular weight standards (lane 2).

Synthetic oligonucleotides may be either end-labeled or synthesized in vitro, with incorporation of a non-radioactive label using methods known in the art. Non-radioactive labels can include, but are not limited to, fluorescent labels or chemiluminescent labels. Fluorescent molecules which can be used to label nucleic acid molecules include fluorescein isothiocyanate and pentafluorophenyl esters. Fluorescent labels and chemical methods of DNA and RNA fluorescent labeling have been reviewed recently (Proudnikov et al., 1996, *Nucleic Acids Res.* 24:4535–42). Chemiluminescent labels and chemiluminescent methods of labeling DNA and RNA have been reviewed recently (Rihn et al., 1995, *J. Biochem. Biophys. Methods* 30:91–102).

In illustrating this embodiment, synthetic oligonucleotides are either end-labeled or synthesized in vitro, with incorporation of biotin-11-UTP into RNA or biotin-16-dUTP into ssDNA or dsDNA during the synthesis reaction as follows. EBNA-1 and Oct-1 DNAs are 82mer and 63mer sequences containing the binding sites for Epstein-Barr virus nuclear antigen (EBNA-1) and Oct-1 protein, respectively, obtained commercially (Pharmacia LKB Biotechnology Inc.—Band Shift Kit). The interleukin-2 (IL-2) enhancer ClaI, HindIII fragment was isolated and purified from the vector 15cxCAT, described previously (Durand et al., 1988, *Mol. Cell. Biol.* 8:1715–1724). DNAs containing 5' overhangs were each incubated with 40 µM biotin-16-dUTP, 20 µM each dATP, dCTP and dGTP, in 10 mM Tris-HCl pH 7.5, 10 mM MgCl$_2$, 50 mM NaCl, 5 mM β-mercaptoethanol and 5 U of the Klenow fragment of DNA polymerase I and in a total volume of 50 µl at 37° C. for 1 hour.

HIV-1 dsDNA PCR products were generated from a template derived from a plasmid containing the HIV-1 long terminal repeat (LTR) and the primer binding site (PBS), (pNLgag) as follows: the DNA including LTR and PBS was cut out from pNLgag using restriction enzymes and then eluted from the gel. The purified LTR (5' U3-R-U5-PBS 3') was used as a template in polymerase chain reactions (PCR), along with synthesized primers complementary to + or − strands of the U3, R or PBS regions of the LTR. These primers also contained either a $T_7$ or Sp6 RNA polymerase site ssDNA. These unique primers were used to generate and amplify dsDNA PCR products that would also incorporate sites for bacteriophage DNA-dependent RNA polymerases on either end. Because the dsDNA PCR products [LTR A (239 bp) and LTR B (690 bp)] incorporated DNA-dependent RNA polymerase sites on either end, they could be used as templates to synthesize RNA in either orientation. $T_7$ or Sp6 RNA polymerase were used with LTR A or B template in RNA synthesis reactions to generate the corresponding labeled or unlabeled RNA. The non-biotinylated LTR A or LTR B-derived RNA could then be used as template(s) to generate the corresponding, complementary, biotinylated, ssDNA HIV constructs. To make ssDNA, RNA was synthesized in vitro using unlabeled ribonucleotides, and then the original PCR-generated dsDNA template was removed with DNase treatment, followed by phenol-chloroform extraction and ethanol precipitation. The purified non-labeled RNA templates were then used to synthesize the labeled, complementary ssDNA in an in vitro reaction containing RNA template, biotin-16-dUTP and dNTPs, along with the corresponding, complementary DNA oligonucleotide primer and Moloney murine reverse transcriptase as described (Sambrook et al., 1989, *Molecular Cloning: A laboratory Manual*). The RNA template could then be removed from the biotinylated ssDNA by RNase H and RNase A treatment. All biotinylated dsDNA, ssDNA or RNA were spun over a chromatographic column (Sephadex G-50) equilibrated in water to remove unincorporated biotin-dUTP or unincorporated biotin-UTP, respectively.

As known in the art, the conditions in a gel mobility-shift assay to promote specific binding between a molecular probe and a nucleic acid binding protein having a recognition sequence specific for binding the probe will depend mainly on the physicochemical and structural properties of the nucleic acid binding protein (see, e.g., Mavrothalassitis et al., 1990, *DNA Cell Biol.* 9:783–8; Werner et al., 1994, *Curr. Biol.* 4:477–87; Erie et al., 1994, *Science*, 266:1562–6).

In this illustration, binding reactions with EBNA-1 extract containing the cloned DNA-binding domain from EBNA-1 protein or Jurkat T cell nuclear extracts prepared as described (Dignam et al., 1983, *Nucleic Acids Res.* 11:1475) and typically greater than 6 ng non-radioactive labeled probe were incubated in 20 mM Tris-HCl pH 7.5, 100 mM NaCl, 1 mM dithiothreital (DTT), 10% glycerol, 0.050% detergent (NP-40) and 50 ng poly(dI-dC) poly(dI-dC) in a total volume of 20 µl for 20 min at 22° C. After the binding reaction, 10–20 µl of the binding mixture was electrophoresed on a 5t acrylamide gel in 1× TBE buffer (Tris-Borate buffer) as described (Sambrook et al., supra). Following depurination, denaturation and neutralization (of gels analyzing DNA only), the DNA or RNA from the gel was transferred overnight onto synthetic membranes (charged nylon membranes; Biodyne B™ membranes, Pall Corp.) using 20× SSC buffer and a positive pressure blotting apparatus (e.g., Posiblot™, Stratagene Corp.) or capillary transfer.

It was found that using the electroblot transfer as previously described for digoxigenin-labeled DNA (Suske et al., supra) resulted in a very variable transfer of the biotinylated-DNA in the retarded complex (DNA+protein extract), with no correlation with the transfer of the biotinylated-DNA probe alone. Positive pressure blot transfer or capillary transfer of biotinylated DNA in the presence or absence of DNA-binding protein onto neutral charge nylon membranes (e.g., Nytran™) also worked poorly, in as much as only the biotinylated DNA in the absence of protein extract transferred to the membrane (data not shown).

Figure 2:
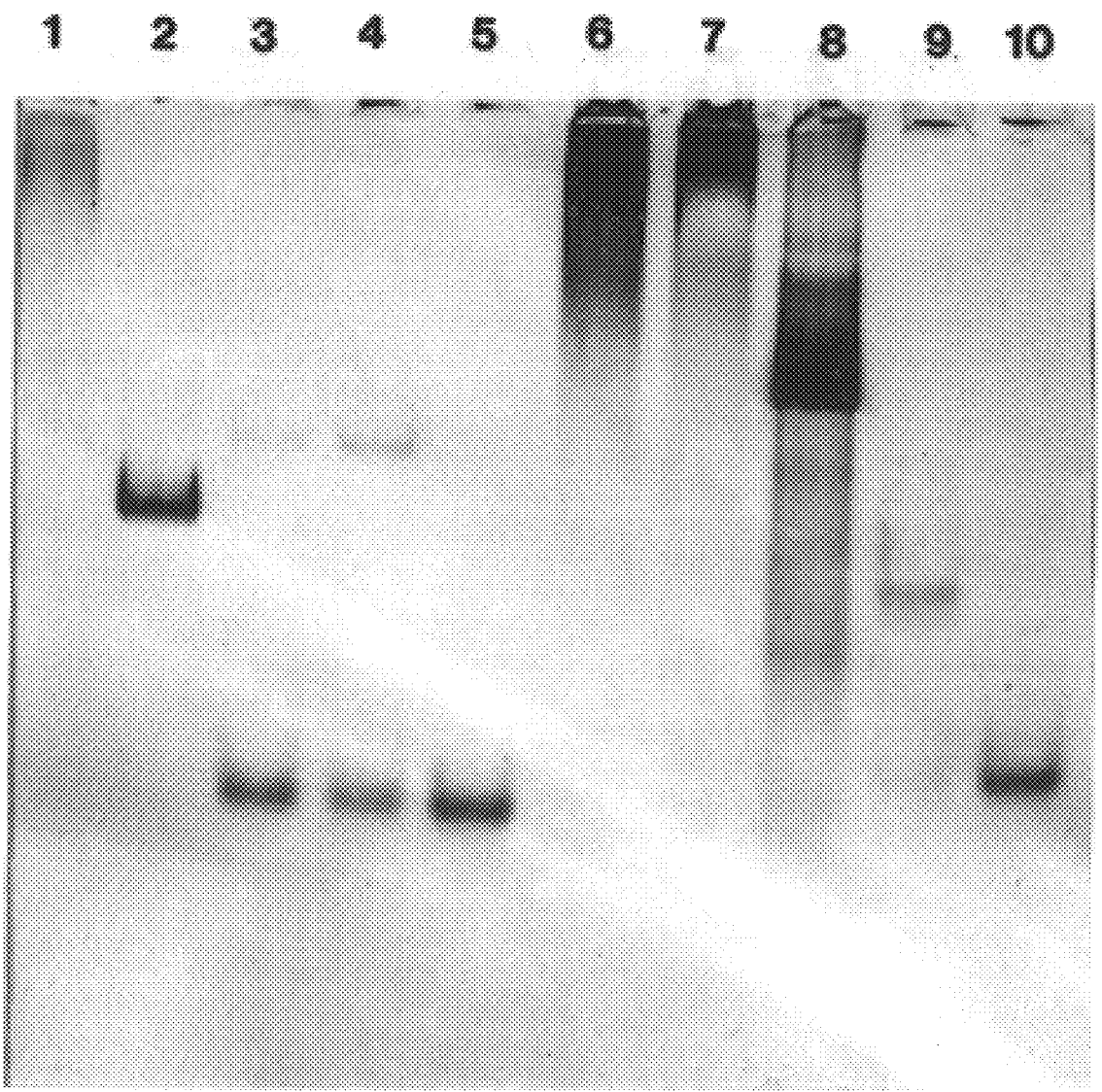
FIG. 2: Comparison of non-radioactive EMSA using variably-sized dsDNA probes; biotinylated IL-2 enhancer (326 bp) in the presence and absence of Jurkat nuclear extract (lanes 1 and 2); biotinylated Oct-1 DNA (63mer) in the presence (lanes 3 and 4) and absence (lane 5) of Jurkat nuclear extract; biotinylated HIV LTR B (690 bp) alone (lane 8) or in the presence of stimulated or control Jurkat nuclear extracts (lanes 6 and 7); and biotinylated EBNA-1 DNA with (lane 9) or without (lane 10) EBNA-1 protein extract.
Figure 3:
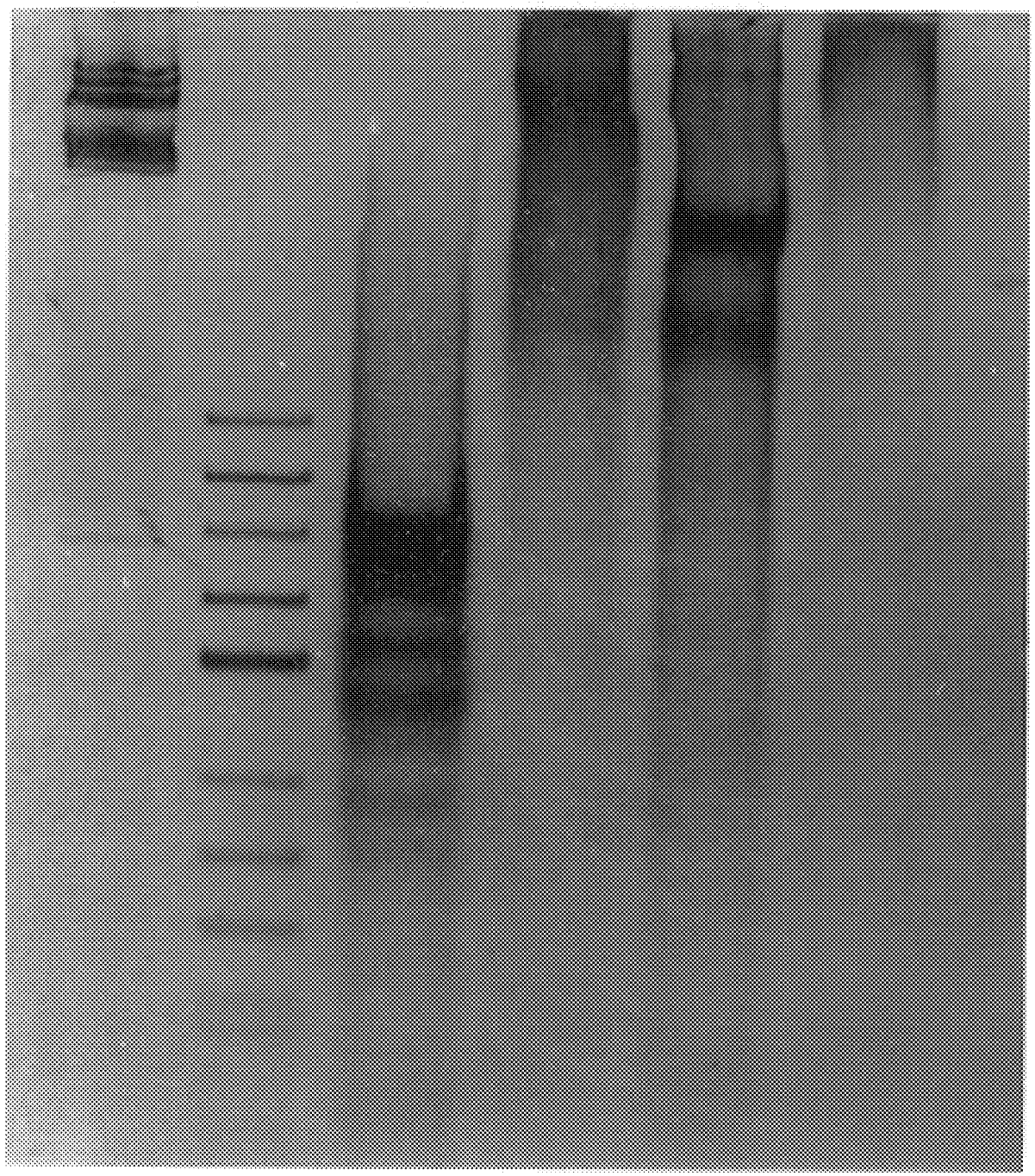
FIG. 3: Biotinylated RNA synthesized by $T_7$ RNA polymerase using HIV LTR A template alone (lane 3) or incubated in the presence of Jurkat nuclear extract (lane 4); biotinylated RNA synthesized from HIV LTR B alone (lane 5) and in the presence of Jurkat nuclear extract (lane 6). Molecular weight standards comprise biotinylated λ HindIII digest (lane 1), and biotinylated low molecular weight standards (lane 2).
Figure 4:
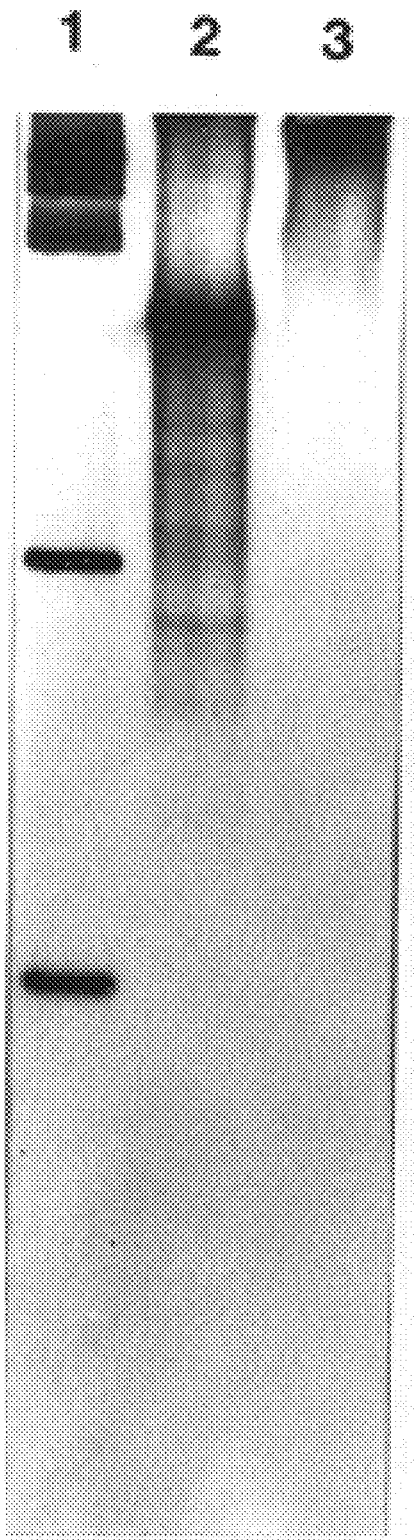
FIG. 4: Biotinylated ssDNA synthesized from HIV LTR B-derived RNA incubated alone (lane 2) or in the presence of Jurkat nuclear extract. The molecular weight standard comprises biotinylated λ HindII digest (lane 1).

The preferred combination in the method of the present invention for efficient and consistent transfer of both non-radioactive labeled molecular probes (alone and in the presence of nucleic acid-binding protein) was to use the combination of positive pressure blot transfer or capillary transfer onto positively charged nylon membranes (FIG. 2). This preferred combination also worked well for biotinylated ssDNA and RNA, as shown in FIGS. 3 and 4. Following UW cross-linking of the DNAs (or RNA) to the membrane using methods known to those skilled in the art, calorimetric detection of the biotinylated DNA or RNA probes on the membrane was performed by blocking, then incubating with Streptavidin-alkaline phosphatase, followed by nitroblue tetrazolium (NBT) and 5-bromo-4-chloro-3-indolyl phosphate (X-phosphate) as described by the manufacturer's instructions (Boehringer-Mannheim, Genius kit).

In other embodiments, a NTP other than UTP or a dNTP other than dUTP can be non-radioactively labeled and incorporated into the oligonucleotide. Additionally, the size of the linkers between a non-radioactive label moiety and the nucleotide labeled may be varied, depending on the nature of the label and the method used for labeling. Further, other synthetic membranes known to those skilled in the art may be used in the present invention, including positively charged or hydrophobic membranes.

What is claimed is:

1. A method for a electrophoretic gel mobility shift assay comprising
   (a) contacting in a mixture a nucleic acid binding protein with a non-radioactive labeled nucleic acid molecule comprising a molecular probe under suitable conditions to promote specific binding interactions between the protein and the probe in forming a complex, wherein said probe is selected from the group consisting of dsDNA, ssDNA, and RNA;
   (b) electrophoresing the mixture;
   (c) transferring, using positive pressure blot transfer or capillary transfer, the complex to a membrane, wherein the membrane is positively charged nylon; and
   (d) detecting the complex bound to the membrane by detecting the non-radioactive label in the complex.

2. The method of claim 1, wherein the non-radioactive label is selected from the group consisting of a fluorescent molecule, a chemiluminescent molecule, and biotin.

3. The method of claim 2, wherein the non-radioactive label is a fluorescent molecule.

4. The method of claim 2, wherein the non-radioactive label is a chemiluminescent molecule.

5. The method of claim 2, wherein the non-radioactive label is biotin.

6. The method of claim 1, wherein the probe is dsDNA.

7. The method of claim 1, wherein the probe is ssDNA.

8. The method of claim 1, wherein the probe is RNA.

* * * * *

UNITED STATES PATENT AND TRADEMARK OFFICE
CERTIFICATE OF CORRECTION

PATENT NO. : 5,900,358
DATED : May 4, 1999
INVENTOR(S) : Linda Besante Ludwig and Barbara J. Hughes It is certified that error appears in the above-identified patent and that said Letters Patent is hereby corrected as shown below:

Title page, inset the following item:

--[60] Provisional application No.60/022,688, July 26, 1996--.

Column 1, line 4, insert the following:

--CROSS REFERENCE TO RELATED APPLICATION

Reference is made to and priority claimed from U.S.provisional application Ser. No.60/022,688, July 26, 1996.

Signed and Sealed this

Twentieth Day of June, 2000

Attest:

Q. TODD DICKINSON

Attesting Officer     Director of Patents and Trademarks